US00PP10757P

United States Patent [19]

Austin

[11] Patent Number: Plant 10,757

[45] Date of Patent: Jan. 19, 1999

[54] SHRUB ROSE PLANT NAMED 'AUSJO'

[75] Inventor: David Charles Henshaw Austin, Albrighton, England

[73] Assignee: David Austin Roses Limited, Albrighton, England

[21] Appl. No.: 799,033

[22] Filed: Feb. 10, 1997

[51] Int. Cl.[6] ..... A01H 5/00

[52] U.S. Cl. ..... Plt./1

[58] Field of Search ..... Plt./1

[56] References Cited

U.S. PATENT DOCUMENTS

P.P. 9,527 4/1996 Austin ..... Plt./1
P.P. 9,705 11/1996 Austin ..... Plt./1

*Primary Examiner*—Howard J. Locker
*Attorney, Agent, or Firm*—Klarquist Sparkman Campbell Leigh & Whinston, LLP

[57] ABSTRACT

A shrub rose plant having a unique combination of large cupped flowers varying from deep yellow in their middles to pale yellow on their outer sides, very strong fragrance, and repeat flowering ability.

1 Drawing Sheet

The present invention relates to a new and distinct variety of shrub rose plant of the rosa hybrida class which was originated by me by crossing 'AUScot' (U.S. Plant Pat. No. 7,215) with 'AUSrush' (unpatented).

The primary objective of this breeding was to produce a new shrub rose variety having greater repeat flowering and shrubby nature and being very resistant to disease. The objective was substantially achieved, along with other desirable improvements, as evidenced by the following unique combination of characteristics that are outstanding in the new variety and that distinguish it from its parents, as well as from all other varieties of which I am aware:

1. Large cupped flowers varying from deep yellow in their middles to pale yellow on their outer sides;
2. Very strong fragrance;
3. Repeat flowers well.

Asexual reproduction of this new variety by budding, as performed at Albrighton, Wolverhampton, England, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'AUScot' (U.S. Plant Pat. No. 7,215).

*Pollen parent.*—'AUSrush' (unpatented).

Classification:

*Botanical.*—Rosa hybrida.

*Commercial.*—Shrub.

Flower

Observations made from specimens grown in a garden environment at Albrighton, Wolverhampton, England in July 1993.

Blooming habit: Recurrent.

Bud:

*Size.*—About 2 inches long when the petals start to unfurl.

*Form.*—The bud form is short, fairly pointed ovoid, broad.

*Color.*—When sepals first divide, bud color is Yellow-Orange Group 20A. When half blown, the upper sides of the petals are Yellow-Orange Group 14B at their base fading to Yellow Group 13D at their upper edges; and the lower sides of the petals are Yellow-Orange Group 15C/D at their base fading to Yellow-Orange Group 18C/D at their outer edges.

*Sepals.*—Color: Yellow-Green Group 144A/B with Greyed-Red Group 181A coloration midline and base. Surface texture: Smooth; leathery. There are three normally appendaged sepals. There are two unappendaged sepals with smooth edges and a few glandular hairs at base.

*Receptacle.*—Color: Yellow-Green Group 144A/B with Greyed-Red Group 182A blush. Shape: Goblet. Size: Medium; slender (about 0.4 inch×0.4 inch) Surface: Smooth.

*Peduncle.*—Length: Medium (about 2 inches). Surface: Slightly glandular. Color: Yellow-Green Group 146C and Greyed-Purple Group 183B. Strength: Stiff, erect.

Bloom:

*Size.*—Medium. Average open size is about 3 inches.

*Borne.*—Singly or several together (1 to 5 per stem). If in clusters: Flattish.

*Stems.*—Medium, normal. Average length is about 24 inches.

*Form.*—When first open: Cupped and slightly globular. Permanence: Flattens slightly, a few outer petals curl back; outer petal edges curl slightly.

*Petalage.*—Number of petals under normal conditions: Variable (55 to 70).

*Color.*—The upper sides of the outer petals are Yellow Group 12A at their base, shading gradually to Yellow Group 12B, thence to Yellow Group 13C in the center and to Yellow-Orange Group 16D at their outer edges; the inner petals are considerably deeper in color. The reverse sides of the petals are Yellow Group 12A at their base, fading to Yellow Group 13C at their center, and thence to Yellow-Orange Group 20C toward the edges. The major color on the upper sides is Yellow Group 13C.

*Variegations.*—None.

*Discoloration.*—The general tonality at the end of the first day: Paler, less orange, Yellow Group 10D. At the end of the third day: Even paler and less orange, Yellow Group 8D.

*Fragrance.*—Strong, very sweet.

Petals:

*Texture.*—Thick.

*Shape.*—Notched at apex, deltoid, heart shaped.

*Form.*—Cupped.

*Arrangement.*—Informal, slightly quartered, with few large petaloids in the center.

*Persistence.*—Petals drop off cleanly before drying.

*Lastingness.*—On the plant: Long (about 5 days). As a cut flower: Not tested.

Reproductive parts:

*Anthers.*—Size: Medium. Quantity: Many. Color: Yellow, Yellow-Orange Group 15A. Arrangement: Tucked in calyx or partly so; mixed with petaloids.

*Filaments.*—Color: Yellow, reddish at base.

*Pollen.*—Color: Gold yellow.

*Styles.*—Color: Greenish white at base, pinkish red at top.

*Stigmas.*—Color: Yellow.

Form: Shrub.

Growth: Vigorous, upright, branching. Mature plant is 3½ feet in height and 4 feet in width.

Foliage: Number of leaflets on normal mid-stem leaves: 5.

*Size.*—Medium (6–7 inches long×5 inches wide).

*Quantity.*—Normal.

*Color.*—New foliage: Upper surface: Yellow-Green Group 147B with Greyed-Purple Group 183B margins. Lower surface: Yellow-Green Group 147C. Old foliage: Upper surface Yellow-Green Group 147A. Lower surface: Yellow-Green Group 147B.

Leaflets:

*Shape.*—Pointed oval, elliptic.

*Texture.*—Upper side: Slightly leathery, smooth, slightly glossy.

*Edge.*—Serrated.

*Serration.*—Single, large.

*Petiole rachis.*—Color: Green.

*Petiole underside.*—Smooth, with prickles (1 to 2 per internode).

*Stipules.*—Medium, serrated; about 1 inch long.

*Disease resistance.*—Resistance to mildew and black-spot under normal growing conditions at Albrighton, Wolverhampton, England.

Wood:

*New wood.*—Color: Yellow-Green Group 146C and Greyed-Purple Group 183B. Bark: Smooth.

*Old wood.*—Color: Yellow-Green Group 146 B. Bark: Smooth.

Prickles:

*Quantity.*—On main canes from base: Ordinary. On laterals from main canes: Ordinary.

*Form.*—Medium, slightly hooked downward.

*Color when young.*—Greyed-Purple Group 183A.

*Position.*—Evenly distributed around stem.

Small prickles:

*Quantity.*—On main stalks: None. On laterals: None.

I claim:

1. A new and distinct variety of shrub rose plant of the rosa hybrida class, substantially as herein shown and described, characterized particularly as to novelty by the unique combination of its large cupped flowers varying from deep yellow in their middles to pale yellow on their outer sides, very strong fragrance, and repeat flowering ability.

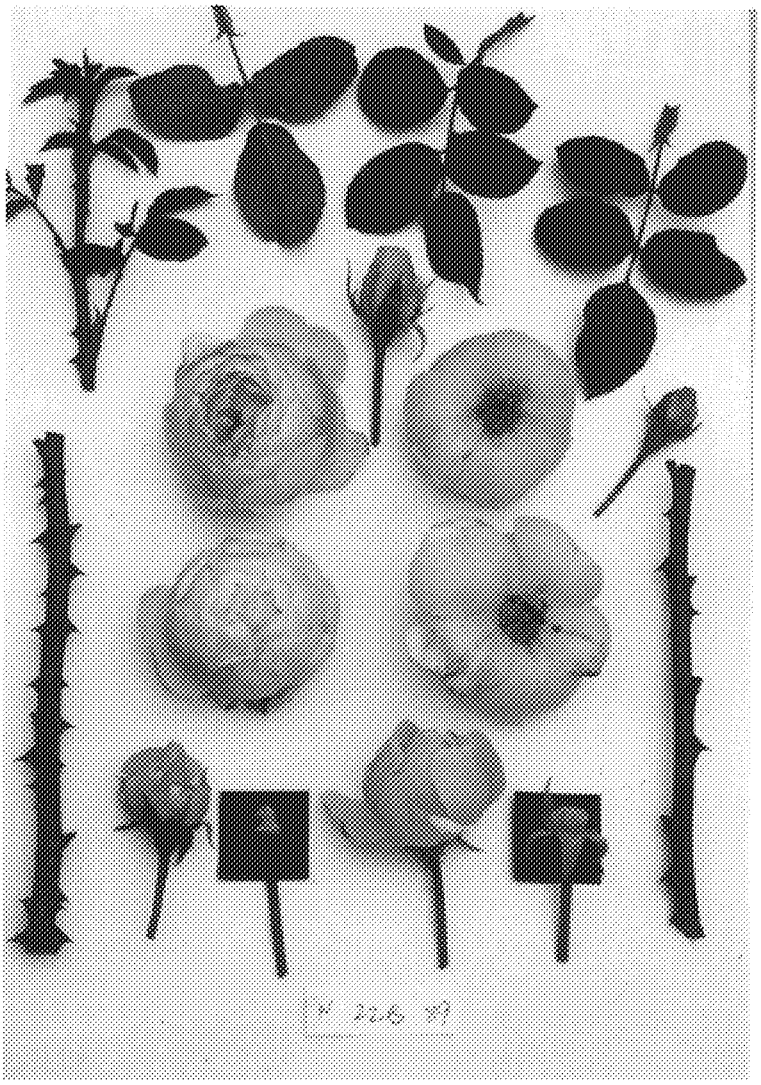

* * * * *